(12) United States Patent
Scholin et al.

(10) Patent No.: US 6,187,530 B1
(45) Date of Patent: Feb. 13, 2001

(54) AQUATIC AUTOSAMPLER DEVICE

(75) Inventors: Christopher A. Scholin, Capitola; Eugene I. Massion, Aptos; David K. Wright, Capitola; Danelle E. Cline, Scotts Valley; Ed Mellinger, Monterey; Mark Brown, Aptos, all of CA (US)

(73) Assignee: Monterey Bay Aquarium Research Institute, Moss Landing, CA (US)

(*) Notice: Under 35 U.S.C. 154(b), the term of this patent shall be extended for 0 days.

(21) Appl. No.: 09/319,333

(22) PCT Filed: Oct. 2, 1998

(86) PCT No.: PCT/US98/20796

§ 371 Date: Jul. 15, 1999

§ 102(e) Date: Jul. 15, 1999

(87) PCT Pub. No.: WO99/18421

PCT Pub. Date: Apr. 15, 1999

Related U.S. Application Data
(60) Provisional application No. 60/060,782, filed on Oct. 3, 1997.

(51) Int. Cl.[7] ............................................. C12Q 1/00
(52) U.S. Cl. ................................ 435/4; 435/6; 435/287.1; 435/288.7; 436/518; 436/164; 436/807; 422/50; 422/68.1
(58) Field of Search ........................ 435/4, 6, 288.7, 435/296, 978, 7.3, 7.36, 291.1, 7.35, 287.1, 32; 436/518, 807, 810, 63, 165, 164; 422/58, 50, 56, 68.1, 102, 72, 101; 210/435, 493.1, 493.5, 787, 791, 794, 348, 416.1

(56) References Cited

U.S. PATENT DOCUMENTS

| 3,869,212 | * | 3/1975 | Burcher et al. . | |
|---|---|---|---|---|
| 3,927,562 | * | 12/1975 | Hickey, Jr. . | |
| 4,502,955 | * | 3/1985 | Schaupp | 210/149 |
| 4,672,039 | * | 6/1987 | Lundblom . | |
| 5,088,499 | * | 2/1992 | Unger . | |
| 5,341,834 | * | 8/1994 | Doherty et al. . | |
| 5,358,690 | * | 10/1994 | Guirguis . | |
| 5,482,626 | * | 1/1996 | Lohnes et al. . | |
| 5,578,459 | * | 11/1996 | Gordon et al. . | |
| 5,658,749 | * | 8/1997 | Thornton . | |
| 5,660,727 | * | 8/1997 | Gleave et al. | 210/141 |
| 5,820,767 | * | 10/1998 | Kane et al. . | |

* cited by examiner

Primary Examiner—Christopher L. Chin
Assistant Examiner—Minh-Quan K. Pham
(74) Attorney, Agent, or Firm—Limbach & Limbach LLP

(57) ABSTRACT

An aquatic autosampler device for frequent collection of discrete samples of microorganisms at various locations and depths. The aquatic autosampler device moves a filter disk within a filter housing from a filter carousel into a filter housing holder. The filter housing holder, slidably mounted on a linear shuttle, moves the filter housing into a process position, where a syringe draws fluid in through a valve manifold and through the filter disk to collect samples on the filter disk. Reagents may then be passed over the filter disk to enable image-based identification and quantification of the cells on the filter disk. An imaging system on the autosampler may capture a fluorescent image of the microorganisms on the filter disk and store the image in a control computer. The filter housing may then be returned to the filter carousel for storage and further lab processing.

24 Claims, 14 Drawing Sheets

AQUATIC AUTOSAMPLER DEVICE

CROSS-REFERENCE TO PROVISIONAL APPLICATION

This application claims priority to U.S. Provisional Application No. 60/060,782, filed Oct. 3, 1997.

FIELD OF THE INVENTION

This invention relates to an aquatic autosampler device. In particular, this invention relates to an autosampler device that permits collection of discrete water samples at many locations and depths for the purpose of quantifying and identifying micro-organisms at more frequent intervals than currently feasible.

BACKGROUND OF THE INVENTION

Understanding the presence, abundance, distribution, and population dynamics of micro-organisms that occur in aquatic environments requires frequent collection of discrete water samples at many locations and depths. Identification and enumeration of particular micro-organisms within those samples typically relies on laboratory-based methods that employ light and/or electron microscopy, and perhaps DNA, lectin, or antibody probes to reveal target species. Collecting appropriate samples over relatively large spatial and temporal scales (e.g., several square miles; months to years) is limited by the frequency one can spend visiting a particular location, and the absolute amount of time one can occupy that location. Similarly, providing quantitative measures of the abundance of a wide variety of micro-organisms that may inhabit those locations is restricted by the time and labor necessary for sample processing. In sharp contrast, many physical, chemical and gross biological properties of the water column may be determined in real-time using a variety of air borne, shipboard, moored and/or drifting sensor arrays. The disparity between the time required to gather and interpret physical and chemical measurements versus the effort to identify and enumerate particular micro-organisms in the same parcel of water, hampers the ability to generate synoptic views of the distribution and abundance of those species in an environmentally relevant context. This in turn impedes the ability to study, either in an applied or academic setting, a wide range of biological phenomena that is occurring at the single cell level, especially within a dynamic aqueous environment.

Molecular probe assays (DNA, PNA (peptic nucleic acid), lectin, or antibody) offer one means to speed and ease the detection and quantification of an enormous variety of organisms, as well the particular genes they harbor and express. However, such applications are presently hindered by the need for highly repetitive operations that demand trained personnel and specialized laboratory facilities. These requirements severely restrict the utilization of molecular probes for real-time ecological studies because the rate of sample processing is inherently limited and application of the technology outside of a laboratory setting is difficult, or more often impossible. U.S. Pat. No. 5,341,834, which is hereby incorporated by reference, discloses a multiport valve for a water transfer system for passing water drawn by a pump through multiple collectors. However, U.S. Pat. No. 5,341,834 discloses no information regarding the use of molecular probes for real-time detection of microorganisms in those samples.

Therefore, novel instrumentation is required if the analytical potential of molecular probe-based assays is to be merged in a synergistic fashion with existing and future capabilities of sensors that measure chemical and physical properties of aqueous environments. For environmental application, such an instrumentation package suitable for detection of micro-organisms should be portable, relatively simple to use, capable of autonomous operation in situ and have the capacity for real-time data transmission. To the best of our knowledge, instrumentation of this class does not exist.

SUMMARY OF THE INVENTION

A new class of instrumentation, an aquatic autosampler, was devised to meet the technological requirements outlined above. This instrument is designed to 1) collect discrete water samples of a known volume autonomously, 2) concentrate particles contained within those samples onto filter disks, 3) automate application of reagents such as preservatives, DNA, PNA, lectin, or antibody probes, and 4) identify and quantify particular species of micro-organisms so captured. Thus, this single electromechanical platform provides the necessary structure for collecting, storing, and processing samples using any one of a number of formats (whole cell or cell homogenate) or molecular probe techniques (DNA, lectin, antibody). The aquatic autosampler collects samples and can process the samples in a variety of ways. The autosampler can process whole cells or cell homogenates and can use different kinds of probes that are either attached to the solid supports, free in solution, or a combination thereof.

The aquatic autosampler has the following major components: a syringe sub-assembly, valve manifolds, reagent bags, a filter carousel having carousel tubes, a filter shuttle, and an imaging system. In operation, a filter disk enclosed within a filter housing is driven up a carousel tube and into the filter shuttle. The shuttle then moves the filter housing into the "process" position, where the sampling takes place. When the filter housing is in the "process" position, the syringe inhales water or other fluid through a valve manifold. The fluid passes through the filter housing and the filter disk, which collects a discrete sample. A toggle valve on the syringe sub-assembly allows the syringe to discharge the fluid, without passing the fluid through the filter a second time, by discharging the fluid through another valve manifold.

Reagents, such as preservatives, detection solutions or molecular probes, contained in the reagent bags may then be drawn across the sample collected on the filter disk, using the syringe. The molecular probes, such as DNA, lectin, and antibody probes, help identify the particular organisms that are present in the sample. The filter shuttle then moves the processed filter to the "unload" position, where an image may be acquired for real-time detection of micro-organisms or, alternatively, the filter housing is sent down a carousel tube for storage and later analysis.

The aquatic autosampler can function inside of as well as outside of a laboratory, and can be moored for autonomous function submerged within the water column when packaged inside a suitable pressure housing. The aquatic autosampler will record results of preprogrammed analytical functions and/or relay that data to a remote location immediately following a process.

BRIEF DESCRIPTION OF THE DRAWINGS

The invention will be better understood by reference to the attached figures in which.

DETAILED DESCRIPTION OF THE INVENTION

Aquatic Autosampler Applications

The aquatic autosampler is applicable to a wide range of research initiatives, both basic and applied. Its principle stand-alone function is to record the presence and abundance of micro-organisms collected in discrete water samples with respect to space and time. With regard to basic research, applications of the aquatic autosampler include groundtruthing of data streams recovered from moored or drifting instrument arrays (e.g., fluorometer, transmissometer, etc.), as well as ocean color satellite images. It can also serve as a tool for studying the growth and distribution of particular microorganisms with respect to aquatic physics and chemistry. In an applied setting, the aquatic autosampler can be used to monitor the quality of drinking water, treated sewage effluent, or serve as a sentinel for early warning of toxic algal blooms that could impact aquaculture operations, etc. It can also serve as a tool for monitoring ships' ballast water to minimize spread of exotic species through ballast water transport and discharge. In summary, the aquatic autosampler can be useful in situations where one wishes to collect micro-organisms in a water sample autonomously and either preserve that material, or apply DNA, lectin, or antibody probe-based assays to detect particular organisms/molecules and relay such data in real-time to a centralized data processing center.

Aquatic Autosampler Design Concept

Figure 1:
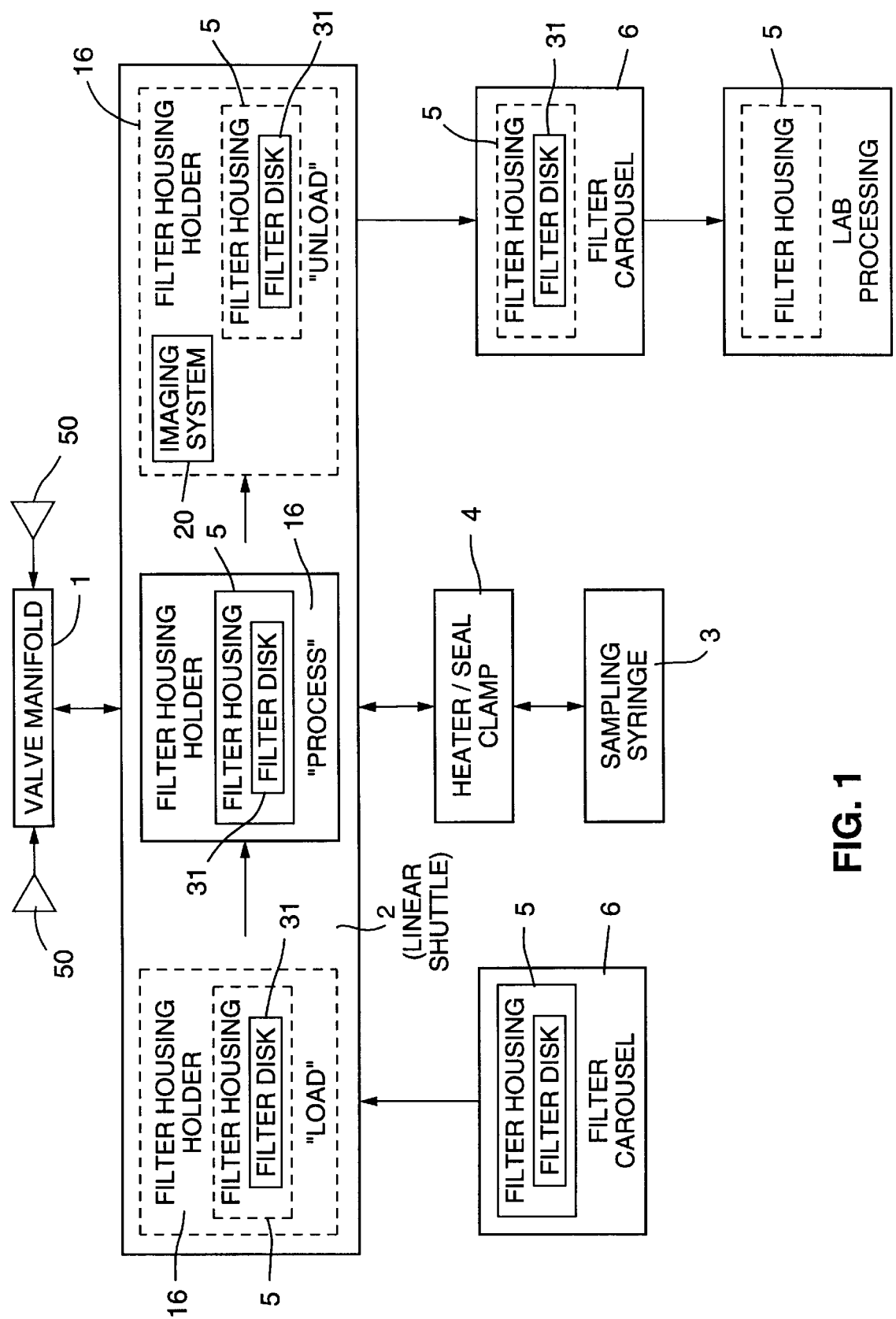
FIG. 1 is a block diagram outlining the aquatic autosampler functions.

A block diagram outlining the aquatic autosampler functions is given in FIG. 1. As envisioned here, the particular species or group of species identified and quantified may be varied by supplying different probes and reagents to a single electromechanical platform. In one embodiment, the aquatic autosampler can collect, archive, and process 90 discrete samples automatically using whole cell or cell homogenate formats, as described in Scholin et al. (1998), Detection and quantification of *Pseudo-nitzschia australis* in cultured and natural populations using LSU rRNA-targeted probes. For autonomous operation, the aquatic autosampler is preferably packaged in a one atmosphere pressure housing 55 and deployed at depths up to ~50 meters for up to ~2 weeks. Data (and/or samples) gathered can be stored on-board the instrument and retrieved at certain intervals or transmitted in real-time depending on the type of sample processing used. It is envisioned that the aquatic autosampler will have expanded sample capacity, and increased maximum deployment depth and duration. Although this instrument is designed to function with complete autonomy, its expressed purpose is to complement and enhance current and expected capabilities of other sensors (e.g., instrument for measuring conductivity, temperature, depth (CTD), acoustic current doppler profiler (ACDP), in situ fluorometer, instrument for measuring partial pressure of carbon dioxide ($pCO_2$), nitrate analyzer ($NO_3^-$), etc.) that would typically be deployed alongside, whether aboard a ship, a moored or drifting platform, or a remotely operated vehicle or autonomous underwater vehicle.

In one embodiment, the aquatic autosampler will collect a known volume of water (e.g., 10–500 ml) using a syringe-based sampler. The syringe 3 itself is relatively small (e.g., 25 ml), and thus large sample volumes require multiple inhalation and exhalation strokes. The volume acquired may be pre-set, or may be varied given the size and porosity of the receiving filter disk 31 or optical properties of the water. The latter could be accomplished using data input from concurrent optical measurements (such as chlorophyll fluorescence and light scatter) to estimate sample biomass and particle loading. Collected water is passed through a filter disk 31 and the filtrate is either discharged or passed to chemical sensor(s) down-stream. Filter disks 31 are shuttled into and out of a filter carousel 6 that houses both fresh and archived (processed) filter disks 31 that are enclosed in filter housings 5. The filter housings 5 are re-usable and will accept a wide variety of commercially available or custom filter disks 31. The choice of filter disk 31 is dictated by the specific mission requirements. The choice of filter disk 31 is based on several factors, including the following: (1) the size of the particles to be filtered, (2) the charge of the particular molecular probe or fluorescence of any moiety attached, and (3) the pH of the solution. Different types of filter disks 31, such as nitrocellulose filters and nylon membranes, are disclosed in Molecular Cloning; A Laboratory Manual, J. Sambrook, E. F. Fritsch, T. Maniatis, 2d ed., (1989), which is hereby incorporated by reference. For some applications, the filter disks 31 have oligonucleotide arrays immobilized on polypropylene supports and are manufactured by Beclanan Instruments. Oligonucleotide arrays are disclosed in U.S. Pat. Nos. 5,549,807; 5,554,501; and 5,583,211, which are hereby incorporated by reference. The use of oligonucleotide microchips is discussed in Guschin et al. (1997), Oligonucleotide Microchips as Genosensors for Determinative and Environmental Studies in Microbiology, which is hereby incorporated by reference.

Particles collected on a filter disk 31 may be subjected to whole cell or cell homogenate analyses. For whole cell analysis, collected cells may be preserved with a chemical fixative and archived as is. Alternatively, prior to archiving, collected cells can be subjected to one or more reagents to apply molecular (DNA, PNA, lectin, or antibody) probes that label specific species (or groups of species) in situ. In either case, preserved whole cells are stored on the filter disk 31 on-board the instrument. The linear shuttle 2 reloads a fresh filter disk 31, staring the process anew. When the instrument is retrieved, the filter housings 5 are unloaded, filter disks 31 removed, and cells examined using light or electron microscopy (the latter requires additional lab-based sample processing, for example, the method described in Miller and Scholin (1996), Identification of cultured Pseudo-nitzschia (Bacillariophyceae) using species-specific LSU rRNA-targeted fluorescent probes). Similar to whole cell-based analyses, a cell homogenate assay begins by collecting a known volume of water onto a filter disk 31. However, collected material is subjected to one or more reagents that lyse (break up; homogenize) cells and liberate their contents. The filter housing 5 is exchanged with one designed to capture particular sequences of nucleic acid in the cell lysate using the principles of sandwich hybridization, as described in Scholin et al. (1998), Detection and quantification of *Pseudo-nitzschia australis* in cultured and natural populations using LSU rRNA-targeted probes. The detection and quantification of such sequences can provide a measure of the presence and abundance of defined target organisms in near real-time, as well as the genes they harbor (genetic capacity) or express. Likewise, the filter disk 31 could be coupled to an antibody and used to capture/detect a specific antigen, with real-time detection following the same principles as that outlined above.

Molecular probes and methods of molecular analysis are well known in the art. Such methods of analysis are disclosed in U.S. Pat. Nos. 5,582,983; 4,851,330; 5,288,611; 5,593,841; 5,541,308; 5,547,842, and PCT application WO 88/03957, which are hereby incorporated by reference. The autosampler allows one to utilize such methods outside of a laboratory autonomously.

System Description

A design of the aquatic autosampler is shown in FIGS. 2–14. The aquatic autosampler is comprised of the following major components: the valve manifolds 1, the linear shuttle 2, the sampling syringe 3, the heater/seal clamp 4, the filter housing 5, the filter carousel 6, the computer-based system controller (not shown) and detection cell (not shown) for optical detection/quantification of colorimetric or chemiluminescent reaction products. With reference to FIG. 1, the filter disk 31, within the filter housing 5, is moved from the filter carousel 6 into the filter housing holder 16 of the linear shuffle 2 at the "load" position. The filter housing holder 16 then shuttles the filter disk 31 and filter housing 5 to a "process" position. At the "process" position, fluid is drawn in by the syringe 3 through the valve manifold 1 from the environment or from reagent bags 50. The fluid is passed over the filter disk 31 to collect samples. A heater/seal clamp 4 at the "process" position may be used to heat the filter housing 5 if necessary for the particular application. After the sample has been taken and processed, the filter housing holder 16 then shuttles the filter disk 31 and filter housing 5 to an "unload" position, where the filter disk 31 and filter housing 5 are sent back into the filter carousel 6 for storage. The filter disks 31 with the collected samples can then be sent to a laboratory for further processing.

Figure 2:
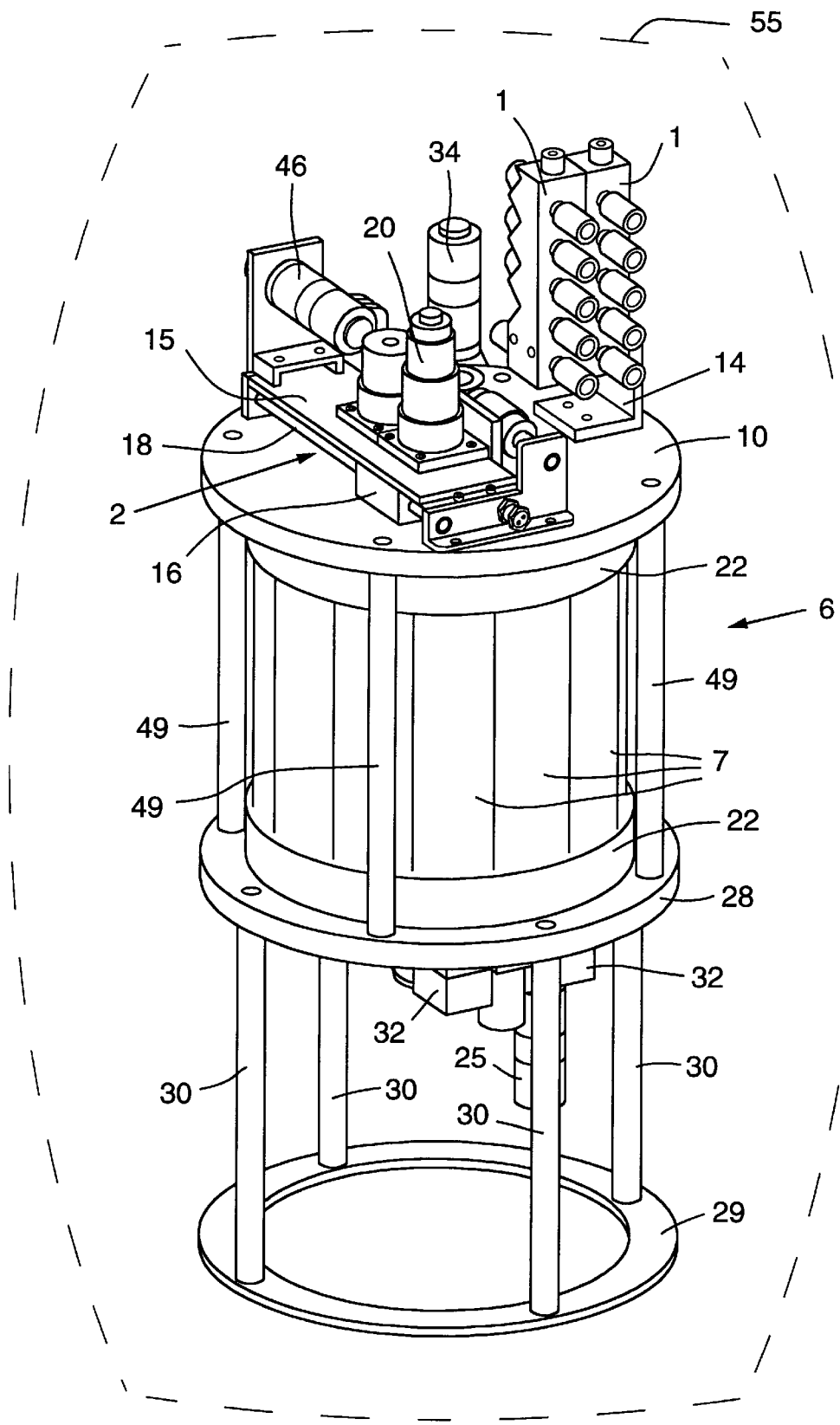
FIG. 2 is a perspective view of the aquatic autosampler.
Figure 3:
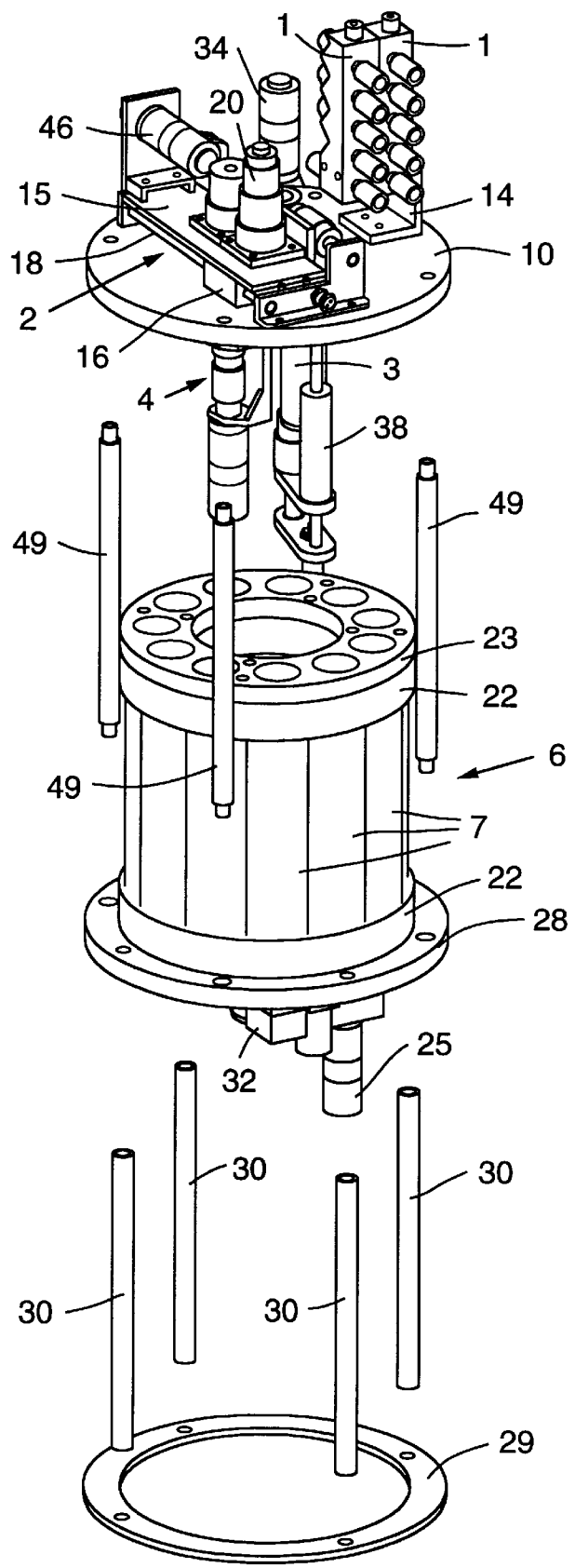
FIG. 3 is an exploded view of the aquatic autosampler.
Figure 4:
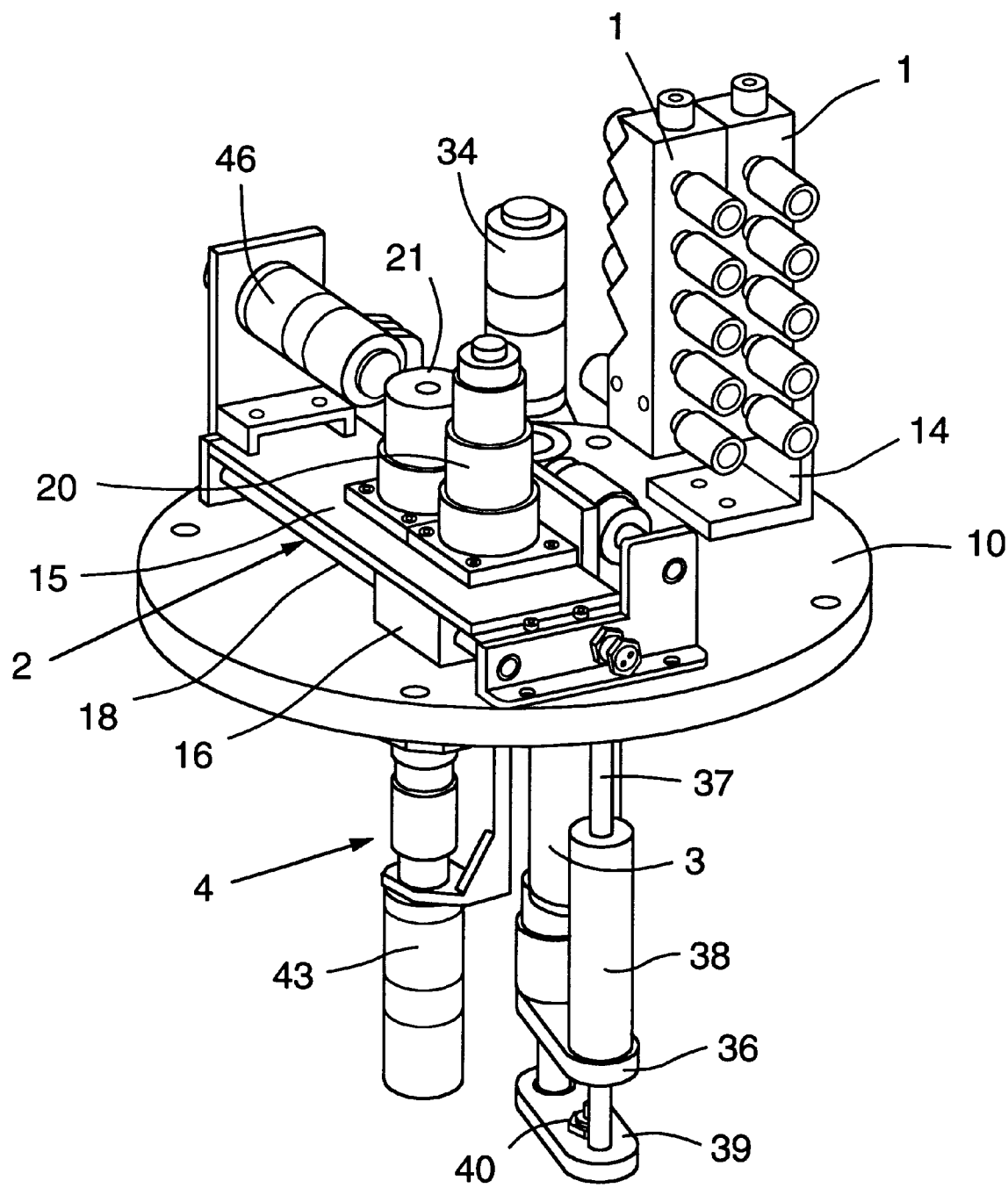
FIG. 4 is a perspective view of the top plate sub-assembly, including the linear shuttle, the valve manifolds, and the syringe.
Figure 5:
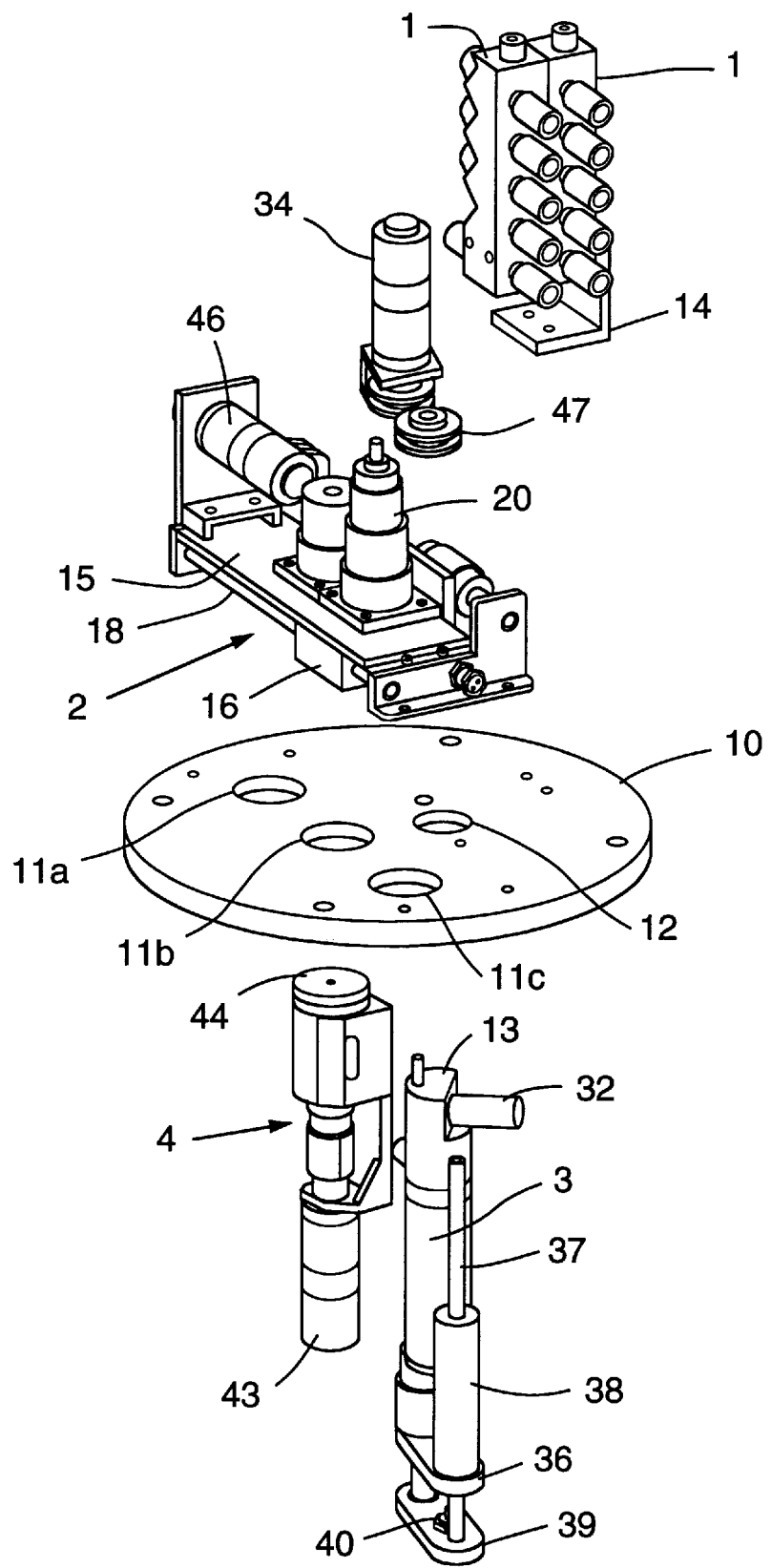
FIG. 5 is an exploded view of the top plate sub-assembly, including the linear shuttle, the valve manifolds, the syringe, and the heater/seal clamp.
Figure 14:
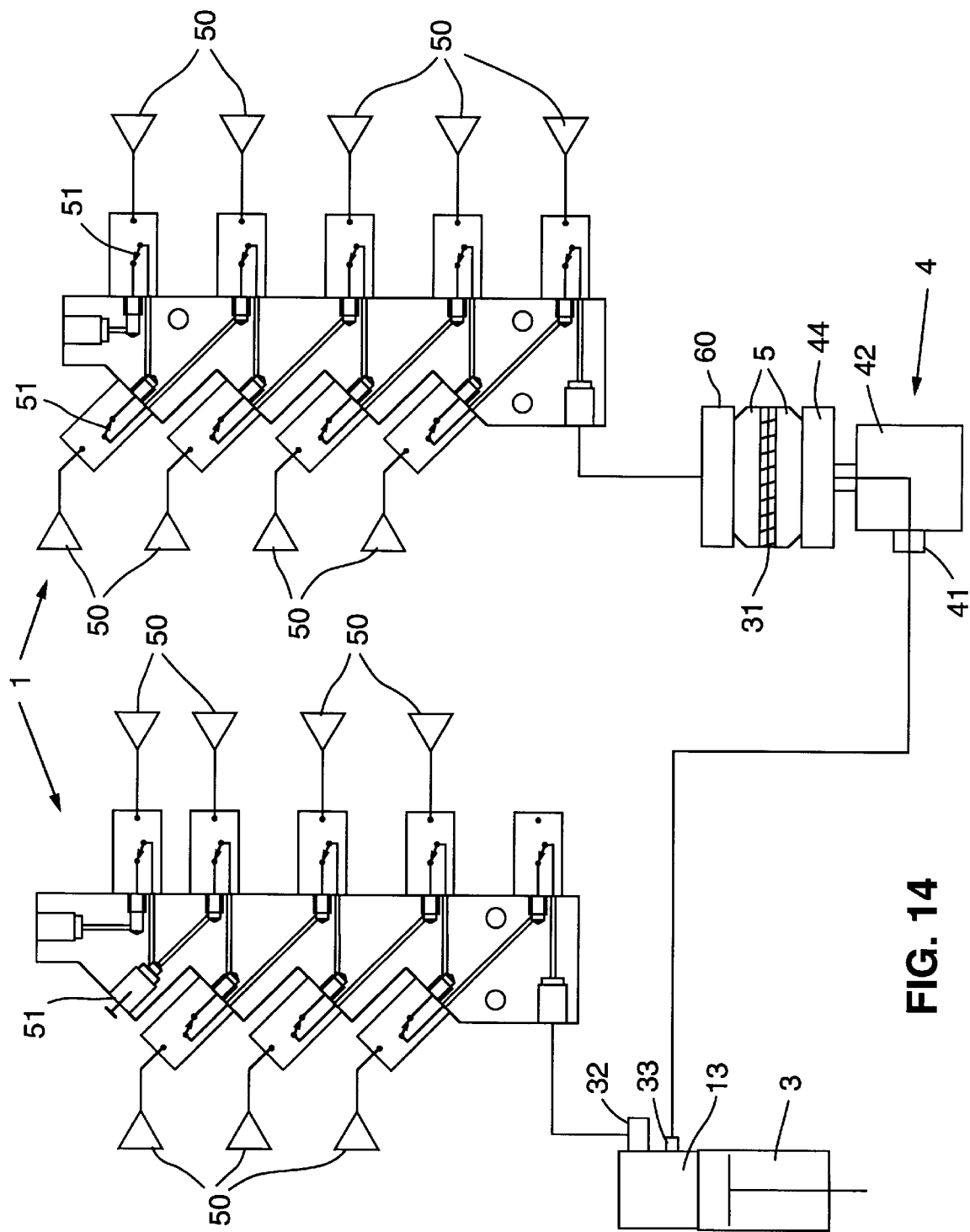
FIG. 14 is a schematic diagram of the fluid flow.

FIG. 2 is a perspective view and FIG. 3 is an exploded view of the aquatic autosampler. FIG. 4 is a perspective view and FIG. 5 is an exploded view of the top plate 10 sub-assembly. Two valve manifolds 1 and the linear shuttle 2 are mounted on the top plate 10. The valve manifolds 1 are arranged side-by-side and mounted to the top plate 10 via a manifold mount bracket 14, as shown in FIGS. 2–5. Reagents and flush fluids are stored in reagent bags 50 which are plumbed to the valve manifold 1, as shown in FIG. 14. The water body to be sampled is also drawn in through a valve 51 on the valve manifold 1.

Figure 10:
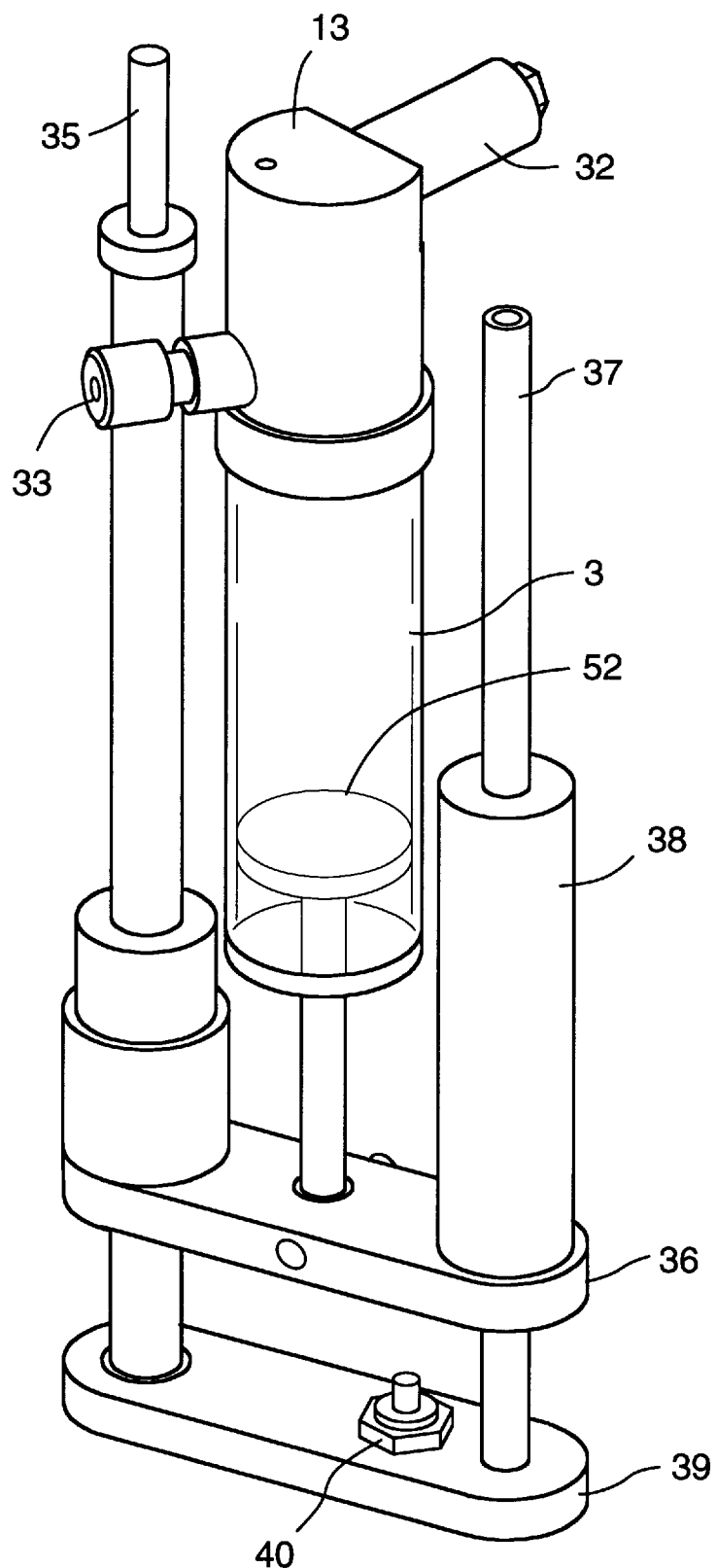
FIG. 10 is a perspective view of the syringe sub-assembly.

As shown in FIG. 5, the top plate 10 is preferably configured with four major openings 11a, 11b, 11c, 12. Three of these openings are filter openings 11a, 11b, 11c and are arranged in a line. The first opening 11a is located at the "load" position and is the opening through which a new filter housing 5 is passed from the carousel tube 7 to the filter housing holder 16 of the linear shuttle 2. The second opening 11b is the opening over the heater/seal clamp sub-assembly 4 and is located at the "process" position. The third opening 11c is the opening through which a spent filter housing 5 is passed from the filter housing holder 16 to an empty tube 7. The third opening 11c is located at the "unload" position. The fourth opening is the opening 12 for the Polyether Ether Ketone (PEEK) manifold 13, which is shown in FIGS. 5 and 10. The linear shuttle 2 is mounted on the top plate 10 over the line of filter openings 11a, 11b, 11c, as shown in FIGS. 4 and 5.

Figure 6:
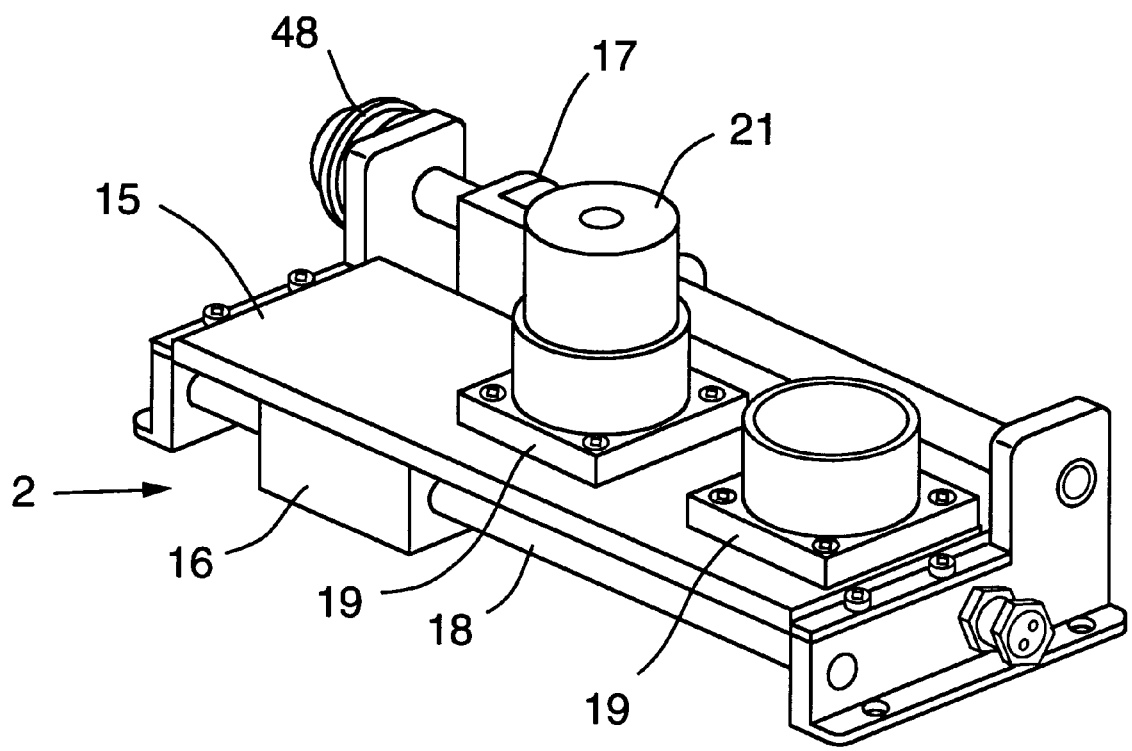
FIG. 6 is a perspective view of the linear shuttle.
Figure 7:
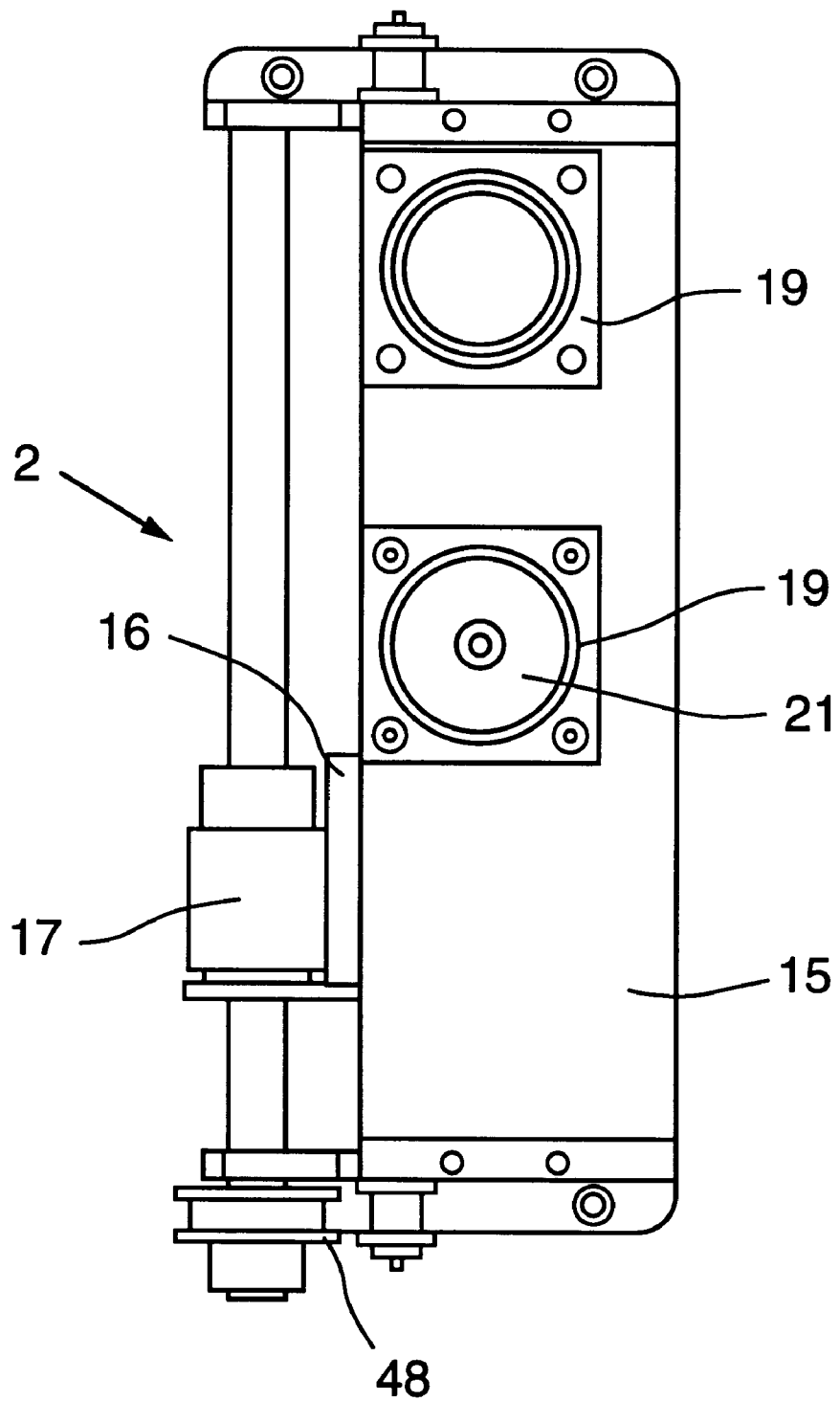
FIG. 7 is a top view of the linear shuttle.

A perspective view of the linear shuttle 2 sub-assembly is shown in FIG. 6. FIG. 7 is a top view of the linear shuttle 2 sub-assembly. The shuttle 2 assembly comprises the following major components: a linear shuttle top plate 15, a filter housing holder 16, a housing guide 17, and a guide rod 18. The filter housing holder 16 is slidably mounted on the guide rod 18. The linear shuttle top plate 15 is configured with two openings, one for a mount boss 19 on which a top heater boss 21, in which may be an upper heater 60 (shown in FIG. 14), may be mounted and one for a mount boss 19 on which an imaging system 20 may be mounted, as shown in FIGS. 4 and 5. The upper heater 60 (shown in FIG. 14) is preferably mounted within the top heater boss 21.

As shown in FIGS. 4 and 5, a linear shuttle motor 46 is mounted on the linear shuttle 2 to slide the filter housing holder 16 along the guide rod 18. The linear shuttle motor 46 is an electric motor driving a belt (not shown) and is connected by a belt to a linear shuttle pulley 48. The pulley 48 in turn rotates a ball-bearing lead screw along which the housing guide 17 is mounted. The housing guide 17 is attached by bracket to the filter housing holder 16, as shown in FIG. 7.

Figure 8:
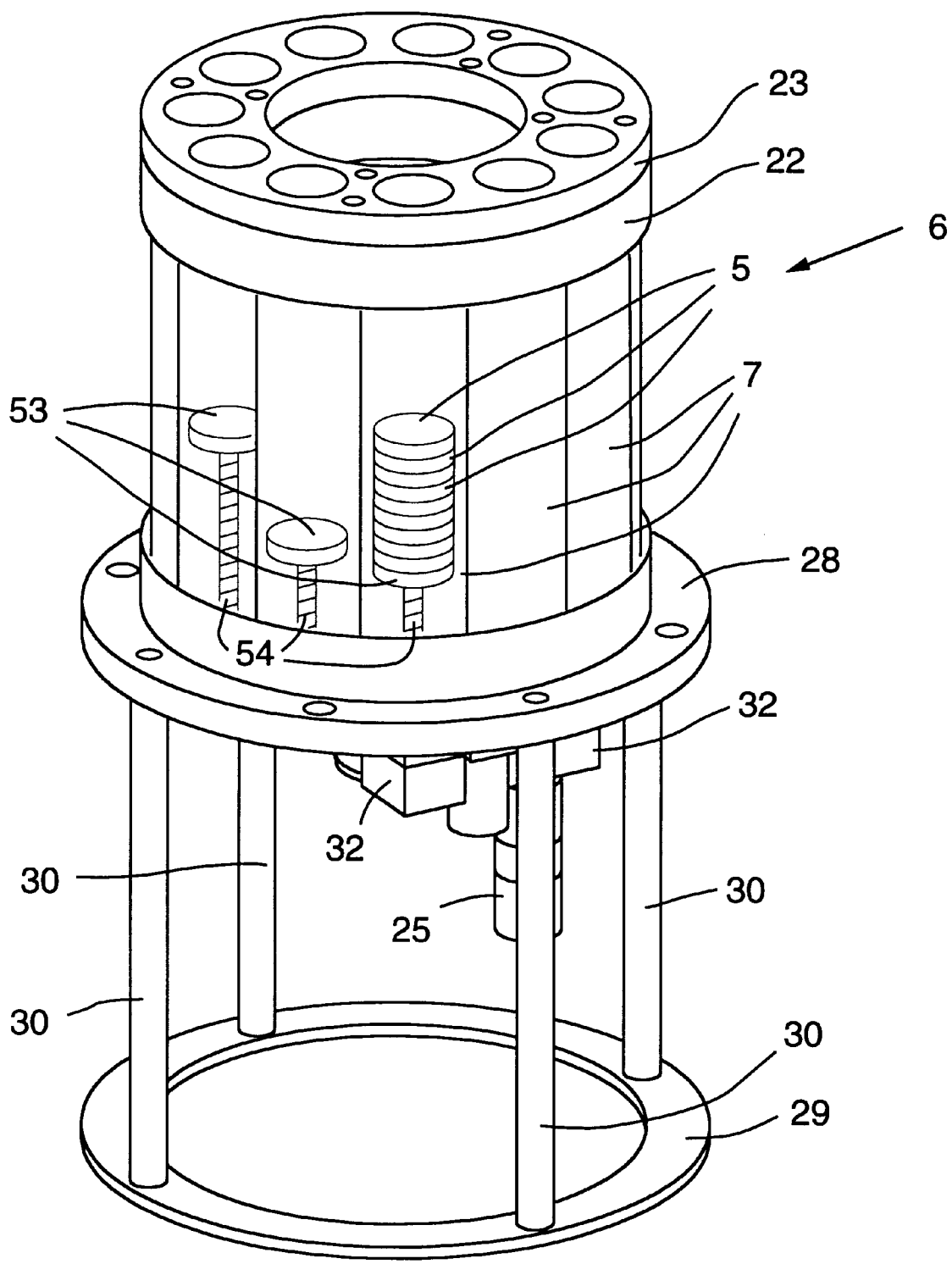
FIG. 8 is a perspective view of the filter carousel.
Figure 9:
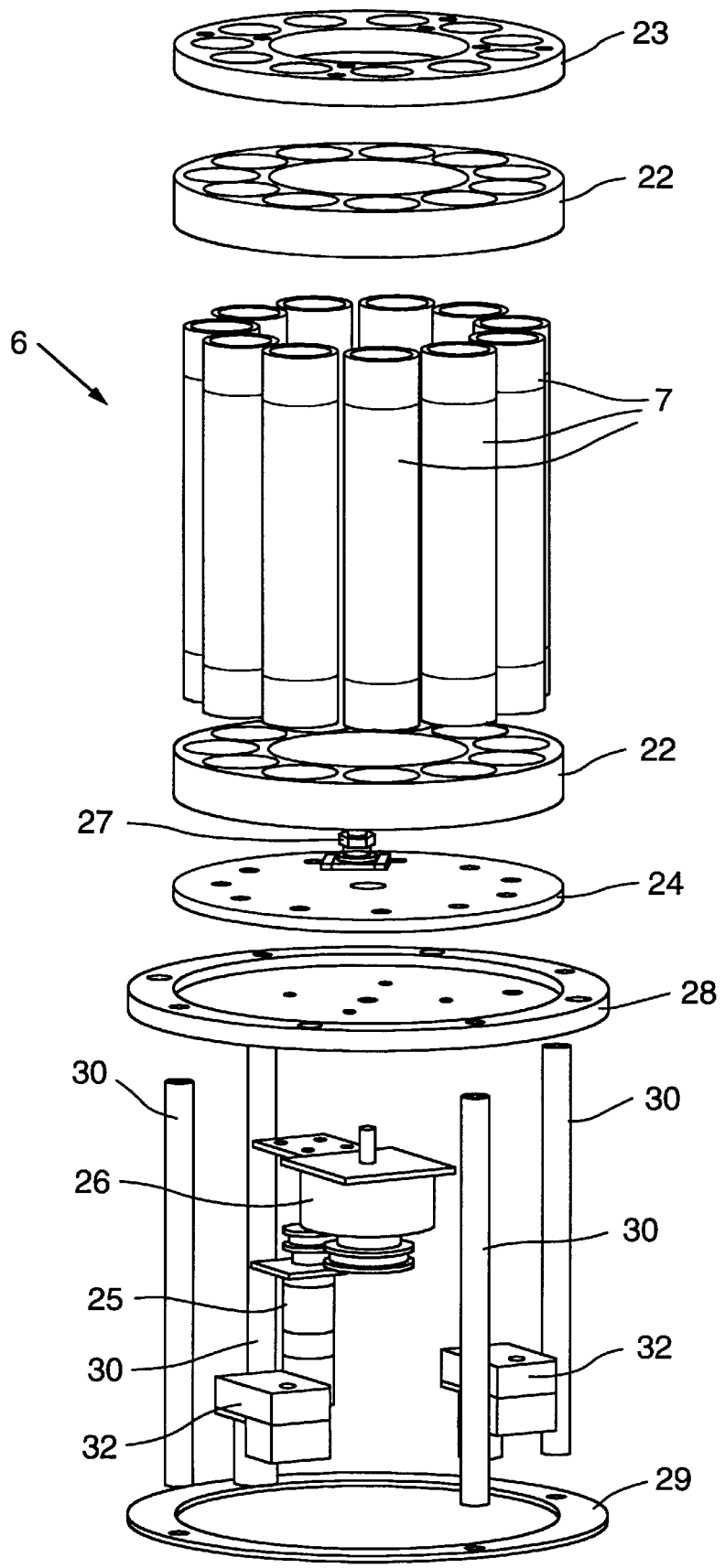
FIG. 9 is an exploded view of the filter carousel.

The rotatable filter carousel 6 is shown in FIGS. 8 and 9. The filter carousel 6 has several vertical tubes 7 for holding stacks of filter housings 5. A filter carousel 6 having several tubes 7 for holding stacks of filter housings 5 makes possible the frequent collection of discrete water samples at various depths, using different filter disks 31 for sampling at different times and /or depths. The tubes 7 are positioned between annular ends 22, which have holes corresponding to the tubes 7. A top bearing 23 is mounted on top of the upper annular end 22 and a bottom bearing 24 is mounted below the lower annular end 22.

As shown in FIG. 9, an encoder 26, mounted to the underside of an upper carousel plate 28, enables exact positioning of the tubes with respect to the filter openings 11a, 11c on the top plate 10. The encoder 26 is driven by a motor 25 and belt drive in a circular direction to rotate the annular ends 22 and the tubes 7. The encoder 26 is coupled to the lower annular end 22 by a coupling 27. The bottom bearing 24 is mounted on the linear shuttle 2 and rests against the upper carousel plate 28, as shown in FIG. 9. The upper carousel plate 28 and a lower carousel plate 29 are connected by support rods 30. The upper carousel plate 28 and the top plate 10 are also connected by support rods 49.

In one embodiment, the carousel 6 has eleven clear acrylic tubes 7 and the upper and lower annular ends 22 and the top bearing 23 each have eleven corresponding holes. In the preferred embodiment, ten of the tubes 7 are filled with stacks of fresh filter housings 5 and one tube 7 remains empty. The initially empty tube 7 is later used to store the used or spent filter housings 5.

As shown in FIG. 8, in each tube 7, a plug 53 supports the stack of filter housings 5. A threaded rod 54 moves the plug 53 up or down within the tube 7. The threaded rod 54 extends through a hole in the bottom of the tube 7. An elevator motor 32, which is mounted on the underside of the upper carousel plate 28, turns the threaded rod 54 to move the threaded rod 54 and the plug 53 up and down within the tube 7. There are two elevator motors 32, one for moving a fresh filter housing 5 up a carousel tube 7 and into the filter housing holder 16 of the linear shuttle 2 and one for receiving spent filter housings 5 from the filter housing holder 16 and down into a carousel tube 7.

Cross-sectional views of the filter housing 5 and filter disk 31 are shown in FIG. 14. The filter housing 5 is formed of a filter disk 31 stacked between layers of frits and seals. In one embodiment, the frits are stainless steel. Some applications would call for frits of other material, such as Teflon. The filter housings 5 may have a clear top, for example, made of acrylic or quartz, such that an imaging system 20 may view the filter disk 31 through the top of the filter housing 5. The imaging system 20 is preferably one that can detect chemiluminescence, fluorescence, or colorimetric reaction products and includes a camera, such as a charge-coupled device (CCD) camera. The imaging system 20 then sends the image of the filter disk 31 to a computer. The imaging system 20 may be mounted on one of the mount bosses 19 on the linear shuttle top plate 15. The imaging system 20 is preferably mounted on the mount boss 19 over the "unload" position such that the image may be taken right before the spent filter housing 5 is sent down an empty carousel tube 7 for storage.

The imaging system 20 may be a fluorescence imaging system, comprising a light source, excitation filter, dichroic beam splitter, emission filter, and a CCD camera. The light source excites the species specific molecular probes in a narrow wavelength band. The probes emit photons at a longer wavelength at an intensity proportional to the amount of species present in the original water sample. The fluorescent image is captured by the CCD camera and stored in the control computer. The computer applies an image processing algorithm to determine the extent to which the probes have labeled target cells or molecules contained within them. The intensity of that signal, and in some cases its location on the filter, is converted to a species concentration using a look-up table and the results are stored in the computer and made available for telemetry to a central processing site. The telemetry aspect of the design would be accomplished using standard radio, microwave, or satellite telemetry.

The syringe sub-assembly is shown in FIG. 10. The syringe sub-assembly comprises the following major components: a syringe 3, a PEEK manifold 13, a toggle valve 32, and a port connector 33. The movement of the piston 52 of the syringe 3 is controlled by a syringe motor 34 that is mounted on the top plate 10, as shown in FIGS. 2 and 3. A belt (not shown) connects the syringe motor to a pulley 47. The pulley 47 of the syringe motor 34 is also part of an electric motor driving belt assembly. The syringe motor 34 is connected to and rotates a ball screw 35. Turning of the ball screw 35 moves a ball nut that is connected to the connector plate 36 so that the connector plate 36 moves slidably up or down along the ball screw 35 and along a guide rod 37. The connector plate 36 is connected to the piston 52 of the syringe 3. Consequently, the piston 52 moves up and down along with the connector plate 36.

A guide bushing 38 is also slidably mounted on the guide rod 37. The guide rod 37 and guide bushing 38 provide additional stiffening and stability to the syringe subassembly when the syringe motor 34 moves the piston 52 of the syringe 3 up and down. The guide rod 37 and the ball screw 35 are anchored on a base plate 39. The connector plate 36 is slidably mounted along the guide rod 37 and the ball screw 35. A limit switch 40 is located on the base plate 39 to limit the movement of the connector plate 36. Preferably, similar limit switches are located at the ends of travel on all rods having slidable elements.

Figure 13:
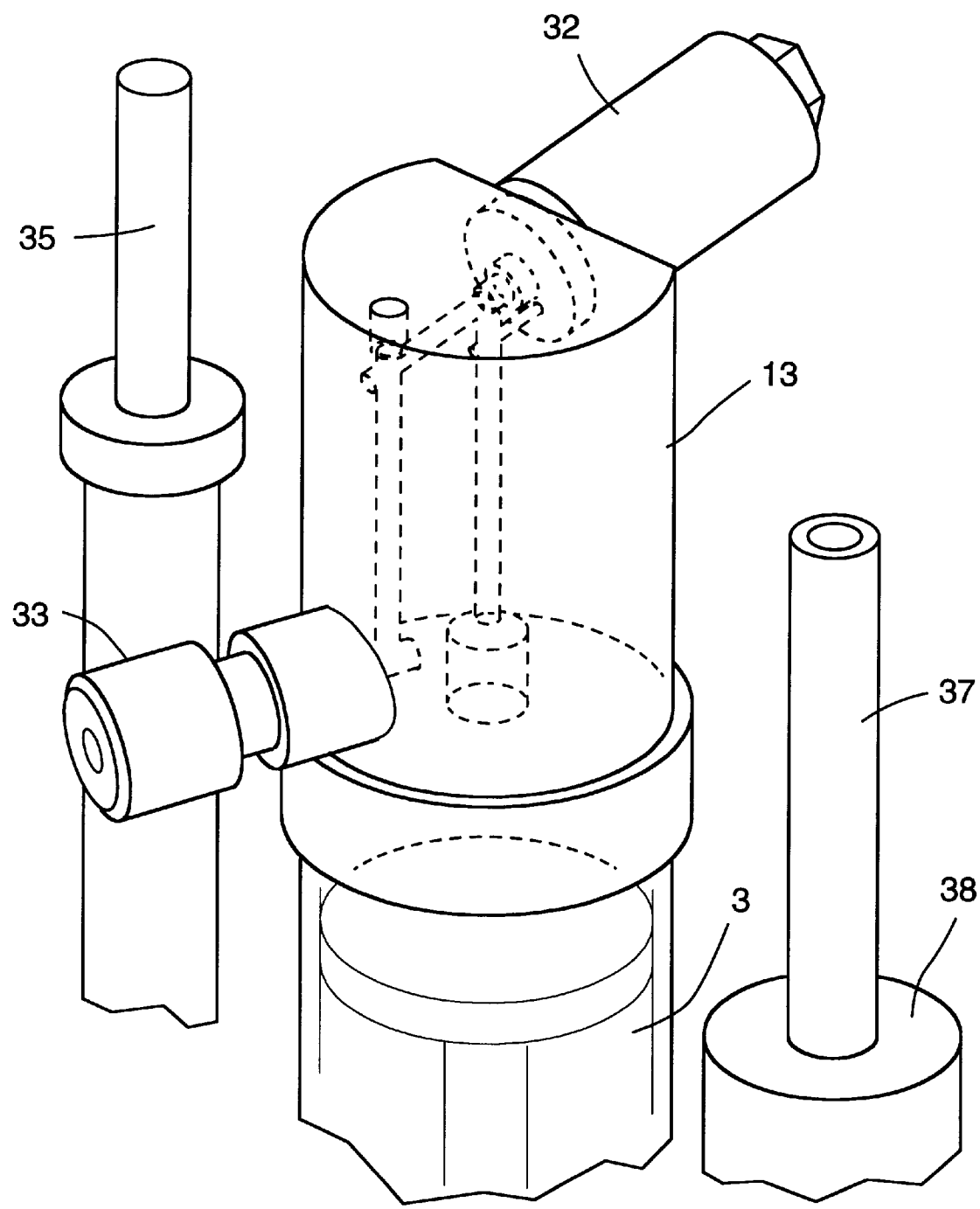
FIG. 13 is a view of the porting run contained in the Polyether Ether Ketone (PEEK) manifold.

The PEEK manifold 13 is mounted on top of the syringe 3. As shown in FIGS. 13 and 14, the PEEK manifold 13 routes the fluid to the heater/seal clamp assembly 4, to the toggle valve 32, and to the syringe 3. The toggle valve 32 is plumbed to the valve manifold 1. The system controller controls the toggle valve 32, which in turn, controls the flow of the fluid and allows the syringe 3 to discharge the fluid without passing it over the filter disk 31 a second time. The PEEK manifold 13 also allows for inhalation of reagents from the valve manifold 1 and for back flushing and mixing of reagents over the filter disk 31.

Incorporated in the system controller are both high speed and low speed communications channels. The high speed channel supports the Ethernet 10baseT interconnect standard, and implements the TCP/IP network protocol. This allows connection to and operation within local and internet networks. The connection may be either by direct, "plugged in" means, or by a wireless/microwave link. The low speed channel is an RS-232D serial port, capable of supporting TCP/IP networking via Point-to Point Protocol (PPP), or any arbitrary serial connection to another computer. This channel may also be directly connected, or be sent through a wireless link.

Regardless of the channel used, a graphical user interface program, executing on a computer that is not part of the autosampler itself, but is in communication with the autosampler, presents data retrieved from the autosampler and sends commands to it. This user interface is required only for human interaction periods of the autosampler's operation. The communication channel is not required to be present during the bulk of a deployment period. Communication may also take place between an automatically executing computer program and the sampler at periodic intervals for the purpose of retrieving data, and generating alert messages to humans, if required. The autosampler itself is capable of operating unattended until its supply of filters, reagents, or data storage capacity is exhausted.

Figure 11:
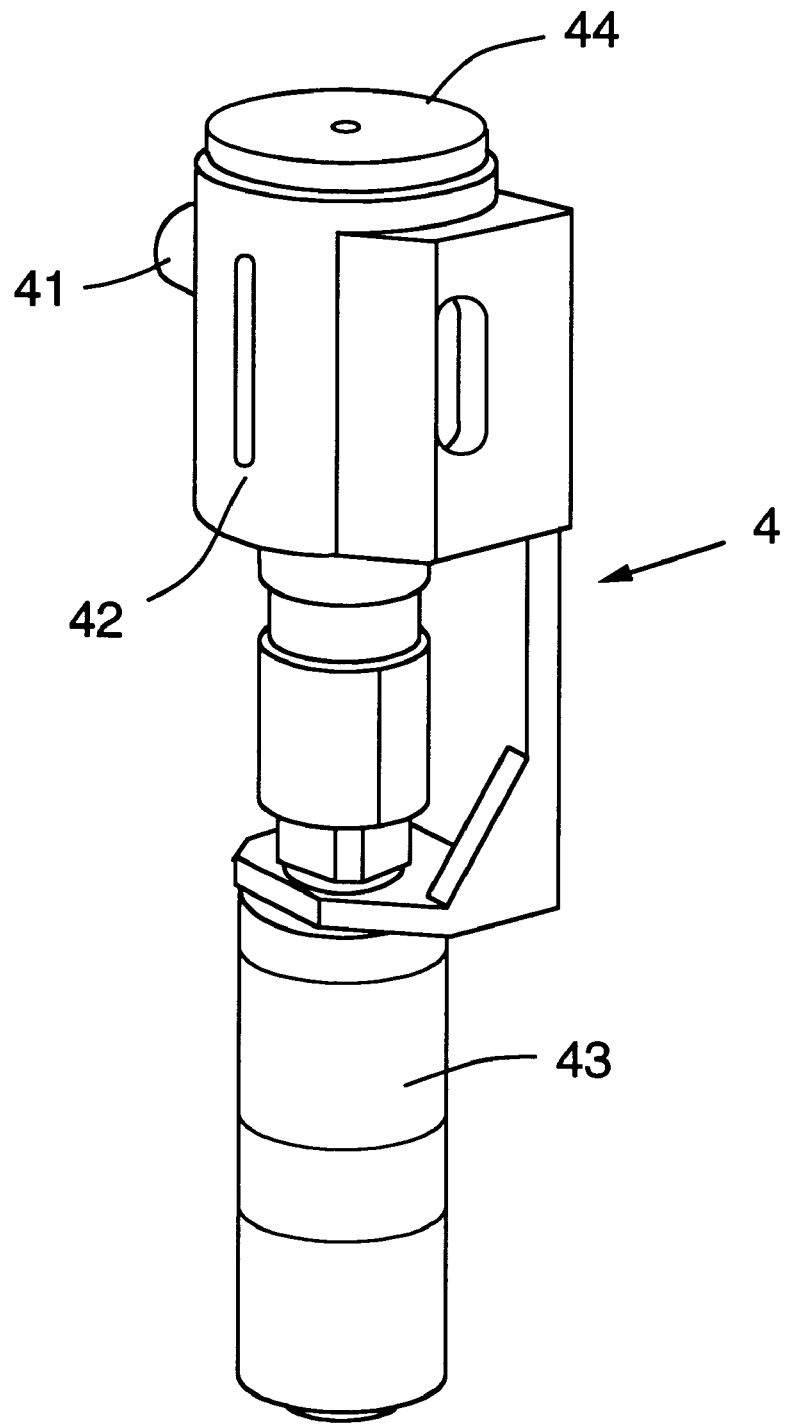
FIG. 11 is a perspective view of the heater/seal clamp sub-assembly.
Figure 12:
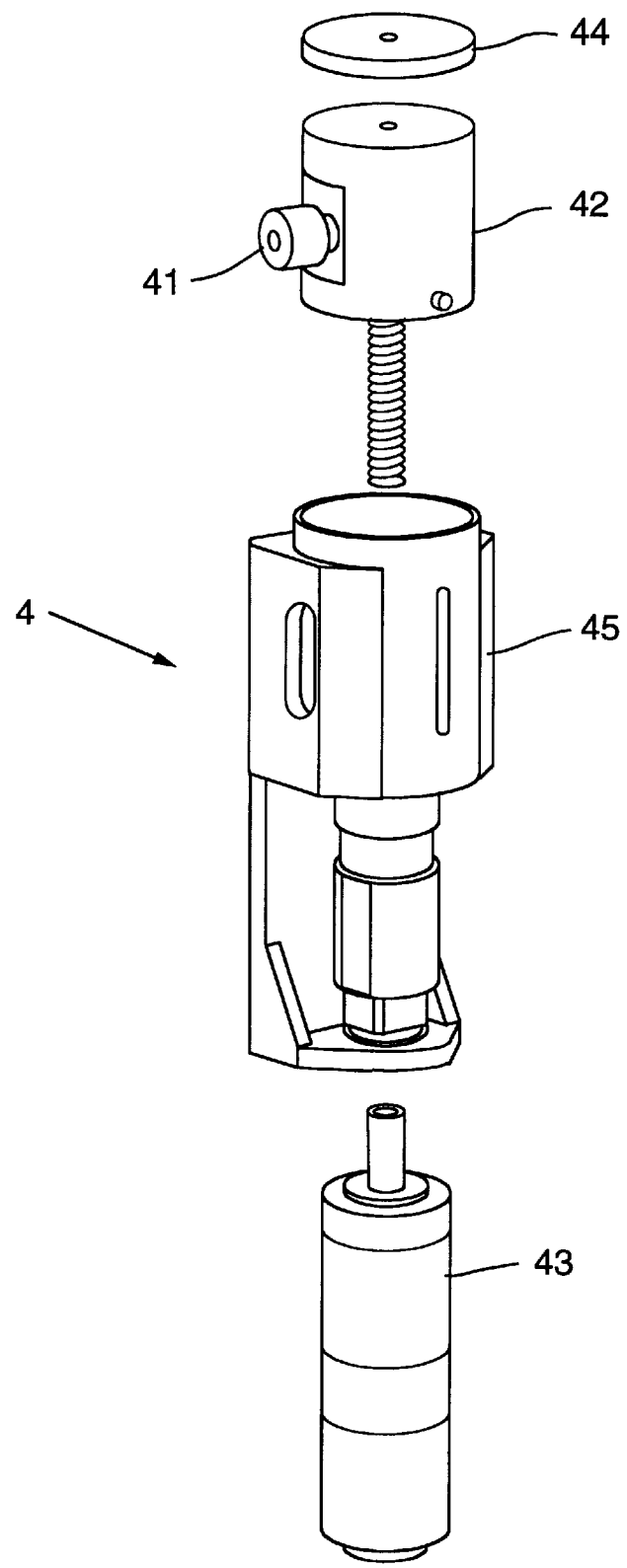
FIG. 12 is an exploded view of the heater/seal clamp sub-assembly.

As shown in the schematic diagram in FIG. 14, the port connector 33 on the PEEK manifold 13 is connected by tubing to a port connector 41 on the heater/seal clamp sub-assembly 4. As shown in FIGS. 11 and 12, the heater/seal clamp sub-assembly comprises the following major components: a lower heater boss 42, a clamp motor 43, a lower heater 44, and a clamp mount 45. As shown in FIG. 12, the lower heater boss 42 fits inside the clamp mount 45. The clamp motor 43 turns to clamp the filter housing 5 tightly between the upper heater 60 (shown in FIG. 14) and the lower heater 44 in the heater bosses 21, 42.

The general procedure for processing samples is as follows. First, the aquatic autosampler is initialized by the computer-based system controller, which controls all of the aquatic autosampler's motors. During initialization, the system controller causes the syringe 3 to be emptied and the syringe piston 52 moved to the bottom of the syringe 3. The system controller also causes the filter housing holder 16 to be moved to the "load" position. The system controller also causes the elevator motors 32 to move the plugs 53 in the tubes 7 to the bottom of the tubes 7.

The filter carousel 6 is then loaded with stacks of fresh filter housings 5. The filter housings 5 are loaded in the carousel tubes 7. All tubes 7 are filled with filter housings 5, except for one tube 7. The empty tube 7 is reserved for storage of spent filter housings 5 with spent filter disks 31.

A filter housing 5 with a fresh filter disk 31 is driven up through the first filter opening 11a in the top plate 10 and moved into the filter housing holder 16 of the linear shuttle 2. The linear shuttle motor 46 then moves the filter housing holder 16 along the guide rod 18 until the filter housing holder 16 is over the second filter opening 11b at the "process" position. At the "process" position, the filter housing 5 is between the heater bosses 21, 42, in which the upper heater 60 and the lower heater 44 are located. The "process" position is where the water sample is passed over the filter disk 31. At the "process" position, the clamp motor 43 clamps the filter housing 5 tightly between the upper heater 60 and the lower heater 44 in the heater bosses 21, 42.

A valve 51 on a valve manifold 1 is then opened to the environment and a water sample is acquired into the syringe 3 and passed over the filter disk 31, retaining particles on the filter disk 31 as the water is pulled through the filter disk 31 as the piston 52 is lowered. The water passes from the valve manifold 1 through the top heater boss 21 and the upper heater 60 to the filter disk 31. Once the water passes through the filter disk 31, it goes through the lower heater 44 into the lower heater boss 42. The water leaves the lower heater boss 42 through the port connector 41. The water then enters the PEEK manifold 13 through the port connector 33 and goes into the syringe 3.

Under some circumstances, the filter housing 5 must be heated by the heaters 44. The temperature of the filter housing 5 is controlled by the system controller. The temperature is preferably displayed in degrees Celsius on a computer.

The syringe 3 can then discharge the water either through the filter disk 31 and out the same valve manifold 1 or through the other valve manifold 1. The toggle valve 32 allows the syringe 3 to discharge the water through the other valve manifold 1. The velocity of the piston 52 of the syringe 3 is also controlled by the system controller.

For whole cell fixation/hybridization/storage, reagents are passed over collected material sequentially. The filter housing 5 containing the sample is then shuttled in the filter housing holder 16 to the "unload" position and archived (stored) back in the filter carousel 6. The "unload" position is lined up with the third filter opening 11c, where the filter housing 5 may be transferred from the filter housing holder 16 to the empty carousel tube 7.

Sandwich hybridization, is broken down into two processes: cell homogenization and target molecule detection. Two types of filters are used for these processes: "sample disk" and "hybridization disk", such as a disk having an oligonucleotide array manufactured by Beckman Instruments. Particulate material is collected onto a sample filter disk as before, but is then subjected to one or more reagents that homogenize (lyse) cells. The sample lysate is ultimately collected into the syringe 3, and the spent sample filter disk is replaced with a hybridization filter disk, using the linear shuttle 2 and carousel 6. The surface of the hybridization filter disk include molecular (DNA, lectin, or antibody) probes that capture target molecules specifically. When the sample lysate is applied to the hybridization filter, target molecules are retained while the rest of the solution passes by. Afterwards, one or more reagents are passed over the membrane, yielding colorimetric, fluorescent, or chemiluminescent products to reveal the presence and abundance of the captured molecules. The process ends with the optical real-time detection of reaction products.

A unique attribute of the aquatic autosampler is that it allows for automated application of a variety of molecular probes for detection and quantification of specific organisms or groups of organisms (depending on the specificity of the particular probe in question) retained on the filter using either whole cell or cell homogenate formats. For example, of the literature references specifically identified below, Scholin et al. (1996a, 1996b, 1998), Miller and Scholin (1996) and Vrieling et al. (1996) have shown that fluorescently labeled species-specific DNA probes are useful tools for discriminating between toxic and non-toxic representatives of Pseudo-nitzschia spp., marine pennate diatoms linked to illness in humans and wildlife. Similarly, Bates et al. (1993) have also demonstrated discrimination of the same organisms using fluorescently labeled antibody probes. In both cases, the DNA and antibody probes are used to identify intact cells. The aquatic autosampler is designed to automate such probe application processes where collection of cells, maintenance of cellular integrity, and exchange of one or more reagents is required to attach a specific probe to the outside, or to subcelluar components inside, of a cell. By attaching such probes, one has the means of identifying an organism as being part of a unique group of species or specific species or strain, even when that organism occurs as one part of complex mixture of other organisms. The aquatic autosampler is also useful for identifying and quantifying a particular species or group of species through application of molecular probes to cell homogenates. In this case, the presence and abundance of a particular organism or group of organisms is gauged by the presence and abundance of a molecule liberated from the intact cell through a suitable lysis procedure. The liberated target molecule is immobilized on a reactive surface where it is subsequently detected and quantified using molecular probes without further reference to cell morphology. An example of the latter type of assay is given by Scholin et al. (1998, 1996a, 1996b) where the application of DNA probes using sandwich hybridization technology was shown a useful means to identify, quantify and discriminate between Pseudo-nitzschia spp., even when the targeted organism(s) occurred in complex samples typical of those found in nature. The aquatic autosampler embodies all of the attributes necessary to conduct cell homogenate assays such these, even when submerged below the water's surface, and has the added capacity to relay results of such tests in real-time to a remote location for subsequent interpretation and analyses.

REFERENCES

The following references, which are hereby incorporated by reference, disclose some of the tests capable of being performed with the aquatic autosampler.

Scholin, C. A., P. Miller, K. Buck, F. Chavez, P. Harris, P. Haydock, J. Howard and G. Cangelosi. 1998. Detection and quantification of *Pseudo-nitzschia australis* in cultured and natural populations using LSU rRNA-targeted probes. *Limnology and Oceanography* (special issue on harmful algal blooms), Vol. 42, No. 5, 1265–1272).

Miller, P. E. and C. A. Scholin. 1996. Identification of cultured Pseudo-nitzschia (Bacillariophyceae) using species-specific LSU rRNA-targeted fluorescent probes. *Journal of Phycology* 32: 646–655.

Scholin, C. A., K. R. Buck, T. Britschgi, J. Cangelosi and F. P. Chavez. 1996a Identification of *Pseudo-nitzschia australis* (Bacillariophyceae) using rRNA-targeted probes in whole cell and sandwich hybridization formats. *Phycologia* 35: 190–197.

Scholin, C. A., P. Miller, K. Buck, F. Chavez, G. Cangelosi, P. Haydock, J. Howard and P. Harris. 1996b. DNA Probe-based detection of harmful algal species using Pseudo-nitzschia species as models. In: Oshima, Y and Fukuyo, Y [Eds.] *Harmful and Toxic Algal Blooms*, Intergovernmental Oceanographic Commission of UNESCO, Paris, 439–442.

Vrieling, E., R. Koeman, C. Scholin, P. Scheerman, L. Peperzak, M. Veenhuis and W. Gieskes. 1996. Detection of a domoic acid-producing Pseudo-nitzschia species in the Dutch Wadden Sea by electron microscopy and molecular probes. *European Journal of Phycology* 31: 333–340.

Bates, S. S., C. Leger, B. A. Keafer and D. M. Anderson. 1993. Discrimination between domoic acid-producing and non-toxic forms of the diatom *Pseudo-nitzschia pungens* using immnunofluorescence. *Marine Ecology Progress Series* 100: 185–195.

F. M. Ausubel, R. Brent, D. D. Moore, K. Struhle. 1987. Current Protocols in Molecular Biology. Massachusetts General Hospital and Harvard Medical School.

Guschin, D. Y., B. Mobarry, D. Proudnikov, D. Stahl, B. Rittmann, A. Mirzabekov. 1997. Oligonucleotide Microchips as Genosensors for Determinative and Environmental Studies in Microbiology. *Applied and Environmental Microbiology*, Vol. 63, No. 6, 2397–2402.

What is claimed is:

1. An aquatic autosampler device, comprising:
   a filter;
   a valve manifold plumbed to the filter;
   a syringe;
   a filter housing positioned to enclose the filter, said filter housing having a first end and a second end, the first end being plumbed to the valve manifold and the second end being plumbed to the syringe, wherein the first end of the filter housing has a heater adjacent and the second end of the filter housing has a heater adjacent; and
   a filter carousel positioned in said device to receive the filter, said carousel having a plurality of filter tubes, the filter carousel being rotatable such that the filter may be moved from one of the filter tubes into the filter housing wherein the filter tubes each have a plug mounted on a threaded rod.

2. The aquatic autosampler device of claim 1 wherein the filter housing is slidably mounted on a rod.

3. The aquatic autosampler device of claim 1 further comprising a plate, wherein the valve manifold and the filter holder are mounted on one side of the plate and the filter carousel and the syringe are mounted on the other side of the plate.

4. The aquatic autosampler device of claim 3 wherein the plate has a load opening for loading the filter from the carousel into the filter holder, a process opening for passing fluid through the valve manifold and the filter into or out of the syringe, and an unload opening for returning the filter to the carousel.

5. The aquatic autosampler device of claim 1 wherein the syringe has a toggle valve.

6. The aquatic autosampler device of claim 1 wherein a pressure housing surrounds the aquatic autosampler device.

7. The aquatic autosampler device of claim 1, further comprising an imaging system.

8. An aquatic autosampler device, comprising:
   a filter;
   a plate having a first side and a second side;
   a valve manifold plumbed to said filter and mounted on the first side of the plate;
   a syringe plumbed to said valve manifold and mounted on the second side of the plate;
   a filter housing mounted on the first side of the plate and positioned to enclose said filter, the filter housing having a first end and a second end, the first end being plumbed to the valve manifold and the second end being plumbed to the syringe, the filter holder being slidably mounted on a rod;
   a filter carousel mounted on the second side of the plate, the filter carousel having a plurality of filter tubes, the filter carousel being rotatable such that the filter may be moved from one of the filter tubes into the filter holder; and
   an imaging system.

9. The aquatic autosampler device of claim 8 wherein the filter tubes each have a plug mounted on a threaded rod.

10. The aquatic autosampler device of claim 8 wherein the syringe has a toggle valve.

11. The aquatic autosampler device of claim 8 wherein the plate has a load opening for loading the filter from the carousel into the filter holder, a process opening for passing fluid through the valve manifold and the filter into or out of the syringe, and an unload opening for returning the filter to the carousel.

12. A method of water sampling, comprising the steps of:
   providing a filter in a position to receive a water sample;
   providing an aquatic autosampler having
      a syringe positioned to sample said water;
      a valve manifold plumbed to said syringe;
      a filter shuttle having a movable filter housing, the filter shuttle having a first boss and a second boss, the first boss being plumbed to the valve manifold and the second boss being plumbed to the syringe, and
      a filter carousel positioned to align with the filter housing the filter carousel having a filter tube, the filter tube having a filter elevator;
   loading the filter into the filter tube;
   rotating the filter carousel to line up the loaded filter tube with the filter holder;
   moving the filter elevator within the filter tube to load the filter housing into the filter holder;
   moving the loaded filter holder such that the filter is between the first boss and the second boss;
   drawing in fluid through the valve manifold into the syringe, the fluid passing through the filter collecting cells in the fluid on the filter; and
   identifying and quantifying the cells on the filter.

13. The method of claim 12 further comprising the step of storing the filter with collected cells in one of the filter tubes.

14. The method of claim 12 further comprising the step of heating the filter.

15. The method of claim 12 further comprising the step of preserving the cells with a chemical fixative prior to identifying and quantifying the cells on the filter.

16. The method of claim 12 further comprising the step of subjecting the cells to one or more molecular probe assays prior to identifying and quantifying the cells on the filter.

17. The method of claim 16 wherein the molecular probe assays are selected from the group consisting of DNA probes, PNA probes, lectin probes, and antibody probes.

18. The method of claim 12 wherein the identifying and quantifying step includes examining the cells using light microscopy.

19. The method of claim 12 wherein the identifying and quantifying step includes examining the cells using electron microscopy.

20. The method of claim 12 wherein the identifying and quantifying step includes examining the cells using a charge-coupled device imaging system.

21. The method of claim 12 further comprising the steps of subjecting the cells to one or more reagents to lyse the cells to liberate cell contents;

replacing the filter with a probe filter, the probe filter having a surface including one or more molecular probes;

passing the fluid over the hybridization filter;

passing one or more reagents over the hybridization filter; and identifying the lysed cells.

22. The method of claim 21 wherein the molecular probes are selected from the group consisting of DNA probes, lectin probes, antibody probes, and peptic nucleic acid probes.

23. A method of fluid sampling comprising the steps of:

moving a fresh filter from a filter carousel into a filter holder in a load position;

shifting the filter holder to a process position in a fluid path;

heating said filter;

drawing a fluid sample through the filter;

shifting the filter holder to an unload position;

moving the filter from the unload position to a spent filter position in the filter carousel and imaging the filter with its collected sample after the filter holder has been shifted to the unload position.

24. The method of claim 23, further comprising the step of drawing one or more reagents through the filter after drawing the fluid sample through the filter.

* * * * *